(12) United States Patent
Sugimoto et al.

(10) Patent No.: US 6,717,609 B2
(45) Date of Patent: Apr. 6, 2004

(54) ELECTRONIC ENDOSCOPE SELECTOR AND ELECTRONIC ENDOSCOPE SYSTEM

(75) Inventors: Hideo Sugimoto, Tokyo (JP); Takayuki Enomoto, Saitama (JP)

(73) Assignee: PENTAX Corporation, Tokyo (JP)

( * ) Notice: Subject to any disclaimer, the term of this patent is extended or adjusted under 35 U.S.C. 154(b) by 452 days.

(21) Appl. No.: 09/756,280

(22) Filed: Jan. 9, 2001

(65) Prior Publication Data

US 2003/0197781 A1 Oct. 23, 2003

(30) Foreign Application Priority Data

Jan. 11, 2000 (JP) .................................. P2000-002673

(51) Int. Cl.[7] .............................. H04N 7/18; H04N 9/47
(52) U.S. Cl. ....................................................... 348/74
(58) Field of Search .............................. 348/65, 66, 72, 348/74, 77; 600/101, 113, 117, 118; H04N 7/18, 9/47; A61B 1/04

(56) References Cited

U.S. PATENT DOCUMENTS

| 5,871,439 A | | 2/1999 | Takahashi et al. | |
| 5,877,802 A | | 3/1999 | Takahashi et al. | |
| 5,929,899 A | | 7/1999 | Takahashi et al. | |
| 5,940,126 A | * | 8/1999 | Kimura | 348/294 |
| 6,306,090 B1 | * | 10/2001 | Wilk | 600/439 |
| 6,584,339 B2 | * | 6/2003 | Galloway et al. | 600/426 |
| 6,597,934 B1 | * | 7/2003 | de Jong et al. | 600/407 |
| 6,602,185 B1 | * | 8/2003 | Uchikubo | 600/118 |
| 2003/0032878 A1 | * | 2/2003 | Shahidi | 600/429 |

* cited by examiner

Primary Examiner—Nhon Diep
(74) Attorney, Agent, or Firm—Greenblum & Bernstein, P.L.C.

(57) ABSTRACT

An electronic endoscope system that shares peripheral devices, such as a TV monitor, VCR etc., among a plurality of electronic endoscopes via an electronic endoscope selector. Each of the electronic endoscopes is connected to the electronic endoscope selector and the electronic endoscope selector selectively switches between video signals of the electronic endoscopes and feeds them to the TV monitor. Further the electronic endoscope selector comprises image memories and is able to store an image captured by the electronic endoscopes. A stored image may be comparatively displayed on the screen of the TV monitor with the live video being captured by the selected endoscope units. Further, the comparative display is controlled by control buttons on the electronic endoscope. The electronic endoscope selector also comprises a memory for storing image parameters for each electronic endoscope, and adjusts images on the screen by utilizing the parameter for each electronic endoscope.

22 Claims, 3 Drawing Sheets

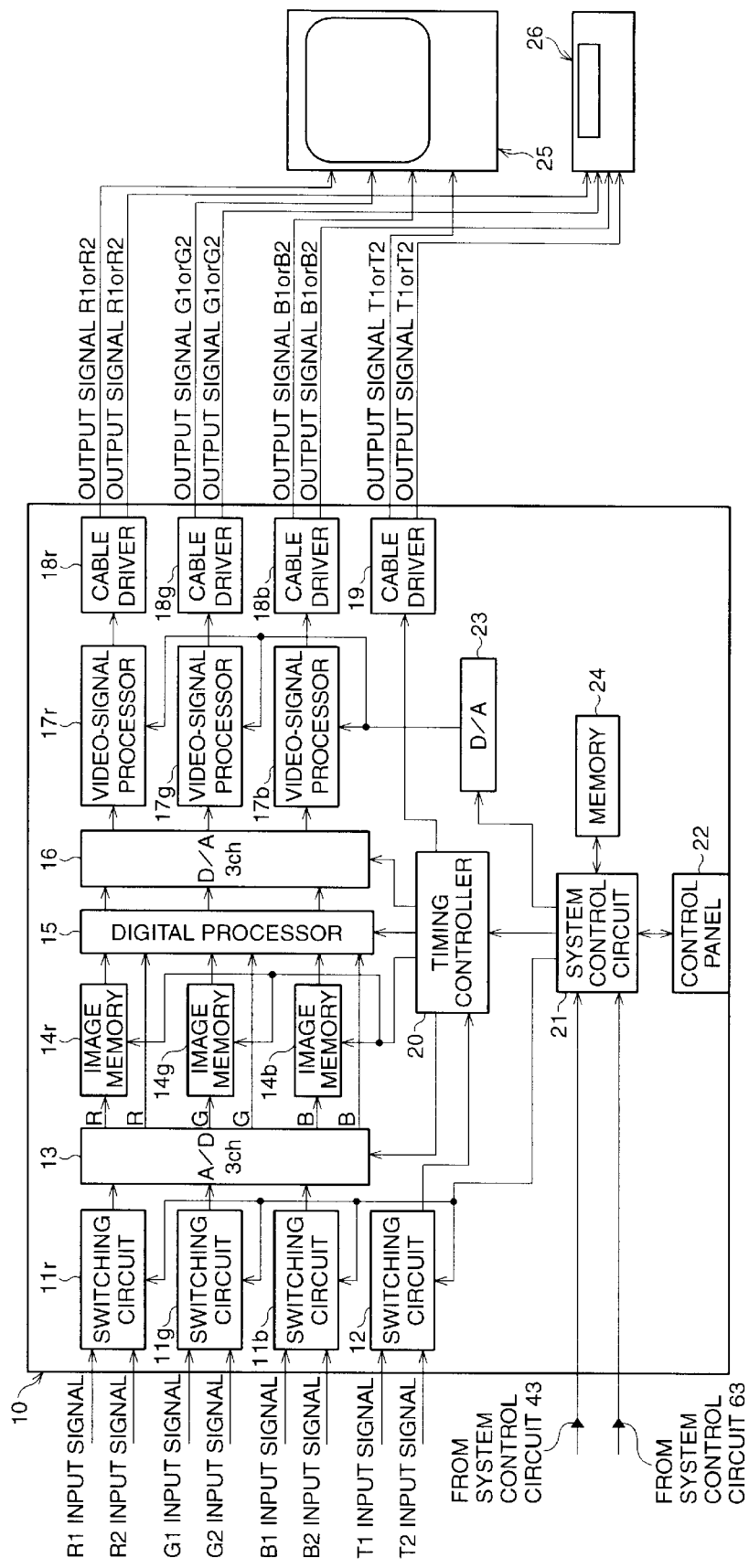

ELECTRONIC ENDOSCOPE SELECTOR
AND ELECTRONIC ENDOSCOPE SYSTEM

BACKGROUND OF THE INVENTION

1. Field of the Invention

The present invention relates to an electronic endoscope system which comprises a plurality of electronic endoscope units and peripheral devices, such as TV monitors, VCR's (video cassette recorder), and the like.

2. Description of the Related Art

In recent medical practice, various types of electronic endoscope systems, such as the RGB sequential or color chip imaging systems, ultrasonic systems, a system that captures a fluorescent image of excited cells in the interior of a hollow organ and so on, are used. An operator may utilize several types of electronic endoscope systems during a medical examination since each type of electronic endoscope system has an exclusive purpose. In electronic endoscopy, captured images are observed by an image indicating device, such as TV monitor and so on. However, when a plurality of electronic endoscope systems are used simultaneously, it is a dissipation of space and cost to provide TV monitors, video cassette recorders and so on, for each electronic endoscope system. It is also cumbersome and time consuming to operate individual peripheral devices for each system.

SUMMARY OF THE INVENTION

Therefore, it is preferable to share devices, such as a TV monitor, video cassette recorder (VCR), etc., that have a common function among the electronic endoscope systems and build a single coordinated electronic endoscope system. In order to share the peripheral devices among a plurality of electronic endoscope systems and build a coordinated electronic endoscope system, an electronic endoscope selector is required that mediates between each of the electronic endoscopes and the peripheral devices.

The above coordinated electronic endoscope system comprises a plurality of electronic endoscope units, each of which comprises an endoscope with an elongated part for insertion into a body cavity or hollow organ, and an image-signal processing unit that processes image signals fed from an imaging device mounted at the distal end of the elongated part of the endoscope.

In a case when several types of electronic endoscope systems are utilized during a checkup or operation, it is quite helpful if images captured by different types of electronic endoscope systems are comparable with each other. For example, in the electronic endoscope system, which captures a fluorescent image of excited cells in the interior of a hollow organ, the electronic endoscope emits shortwave radiation, which includes an exciting wavelength that induces fluorescent of cells, to an unaffected tissue, so that a diagnosis for cancer may be executed while observing a monochrome image displaying the fluorescence of the tissue. However, diagnosis according to the above fluorescent images is not a well-established practice and in order to execute a minute inspection of a suspicious part, cross-reference with normal color images is frequently required. Conventionally, to achieve the above cross-reference between the normal color images and the fluorescent image, the operator needs to interchange endoscopes each time the cross-reference is required. The operator is also required to carry out cumbersome operations to switch images displayed on the screen of the TV monitor, from the images which are fed from one electronic endoscope, to the images fed from another electronic endoscope. Moreover, the frequent interchange of endoscopes compels a patient to endure further unnecessary discomfort.

Therefore, an object of the present invention is to provide an electronic endoscope system that enables a plurality of electronic endoscopes to share a peripheral device and integrate a plurality of electronic endoscope systems into a single coordinated electronic endoscope system. Further, another object of the present invention is to provide an electronic endoscope system which enables stored images captured by one of a plurality of electronic endoscopes, to be comparatively displayed with the live, capturing video.

According to the present invention, an electronic endoscope system is provided that comprises a plurality of electronic endoscopes, a storing medium, an image indicating device, an image storing processor and a comparative images indicating processor.

The image indicating device is for indicating images captured by the electronic endoscopes. The image storing processor stores at least one image captured by one of the electronic endoscopes, in the storing medium as a recorded image. The comparative images indicating processor executes video signal processing, so that a live image being captured by one of the plurality of electronic endoscopes, and the recorded image stored in the storing medium, are comparatively indicated on a screen of the image indicating device.

The electronic endoscope system further comprises an electronic endoscope selector, that selects one electronic endoscope among the plurality of electronic endoscopes and feeds video signals obtained by the selected electronic endoscope to the image indicating device. The electronic endoscope selector can switch one electronic endoscope to another. The recorded image and live image are comparatively indicatable on the screen of the image indicating device by driving the comparative images indicating processor.

Preferably, the storing medium and comparative images indicating processor are disposed in the electronic endoscope selector. Further, the electronic endoscope selector comprises a video-signal processor and an image parameter storing medium that stores image parameters. The video-signal processor executes adjustments for factors relating to tone of the image displayed on the screen of the image indicating device in accordance with the image parameters set for each of the plurality of electronic endoscopes.

Further, preferably, the comparative image indicating processor comprises a first and second image-indicating mode. The first image-indicating mode indicate the recorded image and the live image alternately on the screen of the image indicating device. The second image-indicating mode indicates the recorded image and the live image simultaneously on the screen.

Each of the plurality of electronic endoscopes preferably comprise at least one control switch in order to control the comparative images indicating processor and the image storing processor. Further, preferably, the control switch comprises a first and third control switch. The first control switch controls a storing operation of the image storing processor, and store the recording image captured by one of the plurality of electronic endoscopes in the storing medium. The third control switch controls a switching operation between the first and second image-indicating mode.

The image storing processor may store a plurality of recorded images in the storing medium. Further, the control switch comprises a second control switch that selects one of the plurality of recorded images to indicate the selected image on the screen of the image indicating device.

Further according to the present invention, an electronic endoscope selector that comprises a storing medium, a video signal switching processor, an image storing processor and a comparative images indicating processor, is provided.

The video signal switching processor selectively switches video signal among a plurality of video signals, each of which are fed from a plurality of electronic endoscopes, so that a selected video signal is fed to an image indicating device. The image storing processor stores at least one image captured by one of the electronic endoscopes, in the storing medium, as a recording image. The comparative images indicating processor comparatively indicates images of the selected video signal, or live image, and the recorded image stored in the storing medium.

Preferably, the image storing processor and comparative images indicating processor is controlled by a control signal from the electronic endoscope.

Further preferably, the electronic endoscope selector comprises a video-signal processor that executes adjustment for factors relating to tone of the images displayed on a screen of the image indicating device. The above adjustment may be executed in accordance with image parameters set for each of the electronic endoscopes. The electronic endoscope further comprises an image parameter storing processor that stores the above image parameters.

The recording image stored in the storing medium of the above system or selector is either a still or moving image.

BRIEF DESCRIPTION OF THE DRAWINGS

The objects and advantages of the present invention will be better understood from the following description, with reference to the accompanying drawings in which:

FIG. 4 is a schematic showing an electrical construction of an electronic endoscope selector of the present embodiment.

DESCRIPTION OF THE PREFERRED EMBODIMENTS

Figure 1:
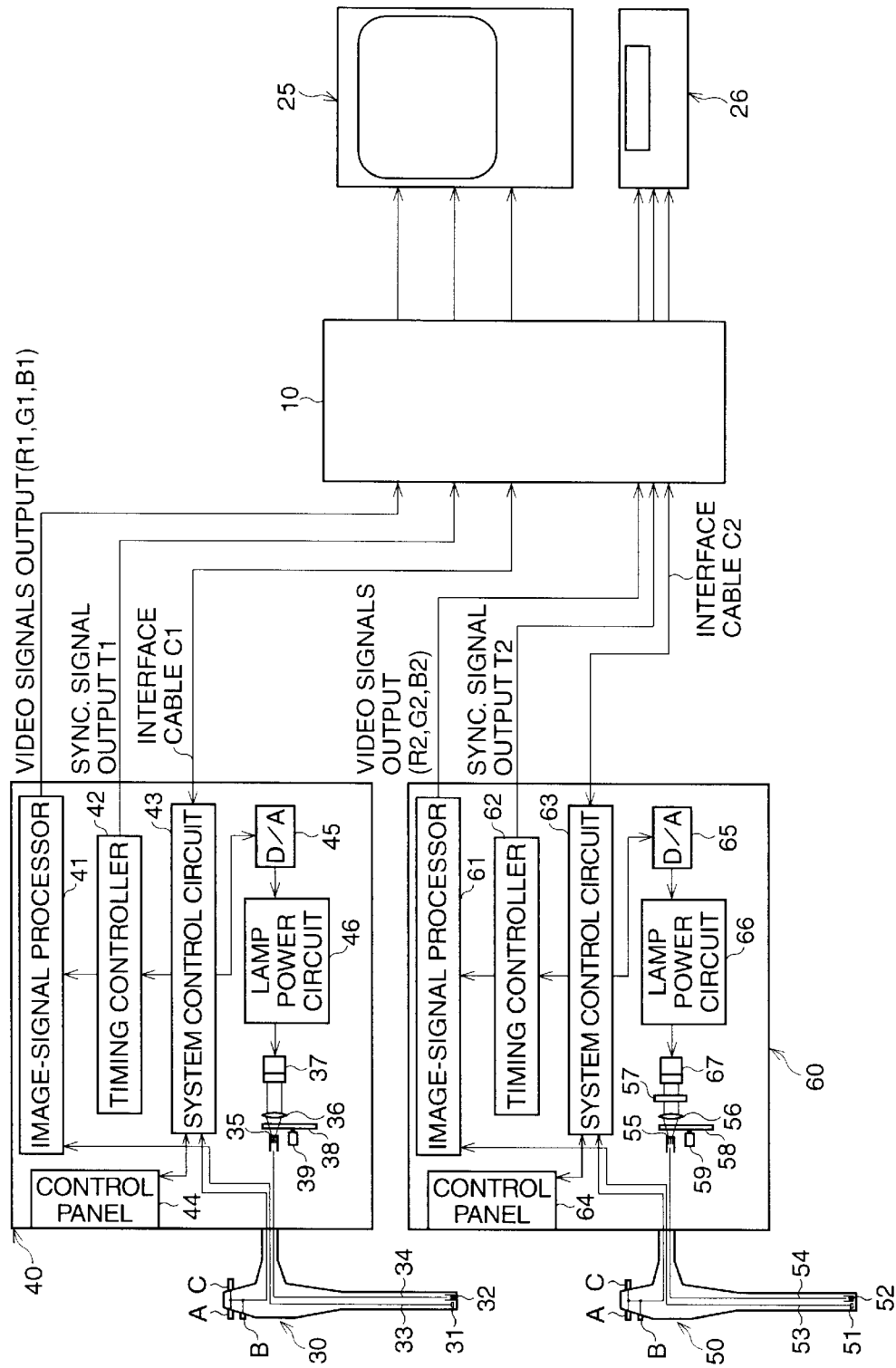
FIG. 1 is a schematic showing an electrical construction of an electronic endoscope system that includes an electronic endoscope selector of the present embodiment of the present invention.

The present invention is described below with reference to the embodiments shown in the drawings.

FIG. 1 is a schematic showing an electrical construction of an electronic endoscope system of the present embodiment. As an example two different types of conventional electronic endoscopes are utilized in the system.

Image-signal processing units 40, 60, the TV monitor (image indicating device) 25 and VCR 26, which are shared by the above two processing units, are detachably connected to the electronic endoscope selector 10 via connectors (not shown). The image-signal processing unit 40 processes image signals for normal color images obtained by a RGB sequential method, utilizing a white light source. The image-signal processing units 60 processes image signals for monochrome fluorescent images obtained by a sequential method that uses shortwave radiation source for illumination. An endoscope 30 is connected to the image-signal processing unit 40 and an endoscope 50 is connected to the image-signal processing unit 60. Each endoscope 30 and 50 is detachably attached to the respective image-signal processing unit 40 and 60 by a scope connector (not shown). On the screen of the TV monitor 25, images captured by the endoscope 30 or 50 are alternatively displayed. The images displayed on the screen of the TV monitor 25 may be simultaneously recorded on a videocassette tape by the VCR 26.

Firstly, a first electronic endoscope unit which comprises the endoscope 30 and the image-signal processing unit 40, and to which the RGB sequential method is applied is described as follows:

In the endoscope 30, the light guide 34, a bundle of extra fine optical fibers, is arranged. An emitting end 32 is arranged at the distal end of the endoscope 30, at one end of the light guide 34. An illuminating lens (not shown) is provided in front of the emitting end 32. Light is emitted from the emitting end 32 and illuminates an object via the illuminating lens. This illumination light is supplied from the lamp (light source) 37, provided inside the image-signal processing unit 40, through the light guide 34, the other end of which is connected to the image-signal processing unit 40 via the scope connector. Note that, there are three control buttons (control switches) A, B and C on the operating handle of the endoscope 30.

Practically, parallel white light is emitted from the lamp 37 and concentrated on the incident end 35 of the light guide 34, via the condensing lens 36, and the RGB rotational filter 38. Light made incident to the incident end 35 is transmitted to the emitting end 32 through the light guide 34 and emitted from the distal end of the endoscope 30 to illuminate the interior of a cavity.

The RGB rotational filter 38 is a flat rotating disk, which has three openings formed at regular intervals in the rotating direction. At each opening, a red (R), green (G) and blue (B) colored filter is attached respectively. The RGB rotational filter 38 is revolved by the motor 39. The rotational axis of the filter 38 is in parallel with the optical axis of the illumination light emitted from the lamp 37. Further, the RGB rotational filter 38 is arranged so that each of the openings traverse the light path when the filter 38 is revolved. Namely, the white illumination light, which penetrates condensing lens 36, passes through each of the R, G, B filters when each opening traverses the light path, and then concentrated on the incident end 35. The illumination light that penetrates the R, G and B filters becomes R, G, B light respectively, and each sequentially made incident to the light guide 34 in regular intervals. Therefore, from the distal end of the endoscope 30, or the emitting end 32, the respective R, G and B light is emitted in regular intervals as illumination light.

The intensity of the lamp 37 is controlled by the lamp power circuit 46 which is controlled by the system control circuit 43. A control signal from the system control circuit 43 is a digital signal. The signal is converted to an analog signal by a D/A converter 45 then fed to the lamp power circuit 46. The revolution of the motor 39 is controlled by a synchronized signal fed from the timing controller 42.

At the distal end of the endoscope 30, an imaging device 31, i.e., CCD, is provided. Image sensing is carried out by utilizing the R, G and B illumination, which is emitted from the emitting end 32. Since the illumination light is periodically emitted in the R, G and B color sequence, images corresponding to each R, G and B component are sensed by the imaging device 31 as sequential monochrome images. Captured images corresponding to each R, G and B component are transmitted as sequential RGB image signals, through the cable 33, to the image-signal processor 41 provided in the image-signal processing unit 40.

Image signals input to the image-signal processor 41 are subjected to prepositional signal processing, i.e., pre-amplifying and video bandwidth filtering, S/H (sample hold), amplifying, clamping, clipping, gamma correction, etc. The image signals are then converted to digital image signals. The digital image signals are temporally stored in the image memories (not shown) for each R, G, and B component as R, G, and B image data. When one set of image data comprising R, G and B images are prepared in the image memories, the R, G, B image data is converted to analog signals and postpositional signal processing is applied. In the postpositional signal processing, a filtering, amplifying, gamma correction, clamping, clipping, enhancing, signal level adjustment process and so on, are executed. The analog image signals are then transformed to the conventional standardized RGB component format or RGB component video signals, and output to the electronic endoscope selector 10.

Timing for driving the imaging device 31, and the image signal processing in the image-signal processor 41, are controlled by synchronized signals fed from the timing controller 42. The timing controller 42 is controlled by the system control circuit 43. Further, the timing controller 42 feeds the synchronization signals to the electronic endoscope selector 10.

The control panel 44, with a switch group (not shown) mounted in the panel, is connected to the system control circuit 43. The system control circuit 43 is connected with the system control circuit 21 (refer FIG. 4) of the electronic endoscope selector 10, via an interface cable C1.

A second electronic endoscope unit, which captures fluorescent images by illuminating the interior of the cavity with shortwave radiation, and comprises the endoscope 50 and the image-signal processing unit 60, is described as follows:

The light guide 54, a bundle of extra fine optical fibers, is provided in the endoscope 50 and one end of the light guide 54, or emitting end 52, is arranged at the distal end of the endoscope 50. An illuminating lens (not shown) is provided in front of the emitting end 52 and shortwave radiation is emitted from the emitting end 52 and illuminates an object via the illuminating lens. This illumination light is supplied from the lamp (light source) 67, provided inside the image-signal processing unit 60, through the light guide 54, which is connected to the image-signal processing unit 60 via the scope connector. Note that, there are three control buttons (control switches) A, B and C on an operating handle of the endoscope 50.

Practically, parallel ultra-violet range light is emitted from the lamp 67. The emitted light passes through an excitation filter 57, condensing lens 57 and rotating filter 58 and is then concentrated on the incident end 55 of the light guide 54. The light, in the range of the exciting wavelength only, is able to pass through the excitation filter 57, therefore only the light in the range of the exciting wavelength is concentrated on the incident end 55. The light made incident to the incident end 55 is transmitted to the emitting end 52 through the light guide 54 and emitted from the distal end of the endoscope 50 as illumination.

The rotational filter 58 is a flat rotating disk and, similar to the RGB rotating filter 38 in the image-signal processing unit 40, has three openings formed at regular intervals in the rotating direction. However, unlike the RGB rotating filter 38, the openings of the rotating filter 58 are unencumbered by filters. The rotational filter 58 is revolved by the motor 59, and the rotational axis of the filter 58 is in parallel with the optical axis of the illumination light emitted from the lamp 57. Further, the rotational filter 58 is arranged so that each of the openings traverses the light path when the filter 58 is revolved. Namely, the illumination light of the exciting wavelength, which penetrates the excitation filter 57 and condensing lens 56, passes through the openings when each opening traverses the light path, and is then concentrated on the incident end 55. Therefore, the shortwave illumination light that penetrates the openings of the rotating filter 58 is sequentially made incident to the light guide 54, and emitted in regular intervals from the distal end, or the emitting end 52, of the endoscope 50.

Intensity of the lamp 67 is controlled by the lamp power circuit 66, which is in turn controlled by the system control circuit 63. A control signal from the system control circuit 63 is a digital signal. The signal is converted to an analog signal by D/A converter 65, then fed to the lamp power circuit 66. The revolution of the motor 59 is controlled by a synchronized signal fed from the timing controller 62.

At the distal end of the endoscope 50, an imaging device 51, such as a CCD, is provided. At the imaging device 51, a monochrome fluorescent image is sensed with the shortwave illumination emitted from the emitting end 52. Although, in the RGB sequential method, monochrome images corresponding to each of the R, G and B colors are sensed, and one set of RGB color images is obtained for each revolution, when capturing fluorescent images which utilize shortwave illumination, only monochrome images corresponding to the exciting wavelength are sensed, since the illuminating light remains a constant excitation light. The captured fluorescent images are fed to the image-signal processor 61, via the cable 53 arranged inside the endoscope 50, as sequential monochrome image signals.

The fluorescent image signals input to the image-signal processor 61 as a set of three images sequentially obtained in one revolution of the rotating filter 58, and are processed in the same way as the RGB image signals obtained in the RGB sequential method. Namely, the fluorescent image signals input to the image-signal processor 61 are subjected to prepositional signal processing, i.e., pre-amplifying and filtering of video bandwidth, S/H (sample hold), amplifying, clamping, clipping, gamma correction, etc., and then converted to digital image signals. A set of digital image signals, corresponding to the three images, is temporally stored in three image memories (not shown) for each image data. When one set of image data, corresponding to the three images, are prepared in the image memories, the image data is converted to analog signals and postpositional signal processing is applied. In the postpositional signal processing, filtering, amplifying, gamma correction, clamping, clipping, enhancing, signal level adjustment processes and so on, are executed. The analog image signals are then transformed to the conventional standardized RGB component format, in other words, RGB component video signals, and fed to the electronic endoscope selector 10. Note that, in this case, each component of the RGB component video signals corresponds to each of the above image signals of the three images. The three images are nearly identical since they are captured in quite a short time. The fluorescent images, as RGB component video signals from the second electronic endoscope unit, are displayed on the screen the TV monitor 25 as monochrome images.

Timing for driving the imaging device 51, and the image signal processing in the image-signal processor 61, is controlled by synchronized signals fed from the timing controller 62. The timing controller 62 and the image-signals processor 61 are controlled by the system control circuit 63. Further, the timing controller 62 feeds the synchronization signals to the electronic endoscope selector 10.

The control panel 64, with a switch group (not shown) mounted in the panel, is connected to the system control circuit 63. Further, the system control circuit 63 is connected with the system control circuit 21 (refer FIG. 4) of the electronic endoscope selector 10, via an interface cable C2.

Figure 2:
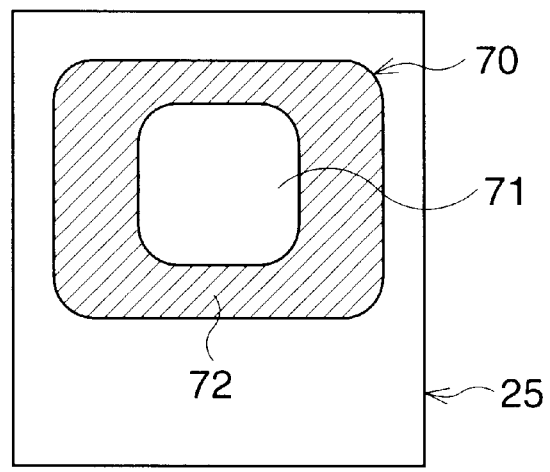
FIG. 2 illustrates a display arrangement on the screen of a TV monitor in the one-image indicating mode (first image-indicating mode) of the present embodiment.
Figure 3:
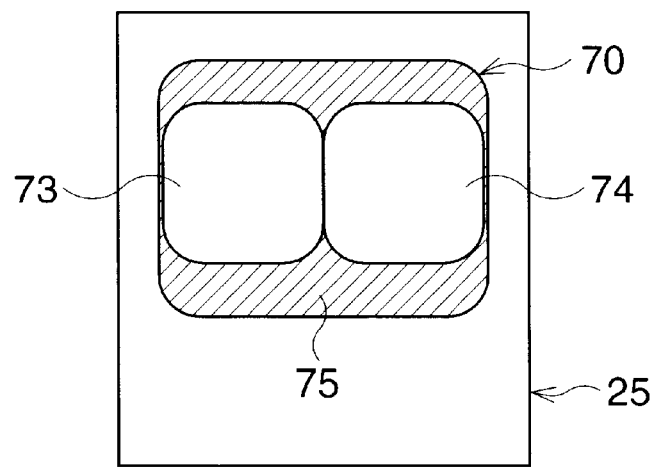
FIG. 3 illustrates a display arrangement on the screen of the TV monitor in the two-image indicating mode of the present embodiment.

With reference to FIG. 1 through FIG. 3, functions for the control buttons A, B and C arranged on the operating handle of each endoscope 30 and 50, are explained.

The control buttons A, B, C are connected to the system control circuits 43 and 63 of the image-signal processing units 40 and 60, respectively, with cables. When the control buttons A, B, C on the endoscopes 40 or 60 are operated, corresponding operating signals are send to the respective system control circuit 43 or 63 and control signals corresponding to the operating signals are output from the system control circuits 43 or 63. The control signals from the system control circuits 43 and 63 are fed to the system control circuit 21 (refer FIG. 4) of the electronic endoscope selector 10 via interface cables C1 and C2. At the electronic endoscope selector 10, video signals are processed in accordance with the above control signals and output to the TV monitor 25 and VCR 26.

Initially, as shown in FIG. 2, images from a selected electronic endoscope unit are displayed on an image indicating area 71, which is a part of a screen 70 of the TV monitor 25. Namely, video being captured by the endoscope 30 or 50 is displayed on the image indicating area 71 as the live image in real-time. Note that, in this embodiment, the number of pixel in the imaging device 31, 51 is smaller than that in the screen of the TV monitor 25, thus there is margin, an area where no image is displayed, indicated as a hatched portion 72.

A color or fluorescent image, which is comprised of a set of RGB or three monochrome images captured by an electronic endoscope, is stored in respective image memories (storing mediums) 14r, 14g and 14b of the electronic endoscope selector 10 (refer FIG. 4), when the control button A of a selected electronic endoscope unit is pressed. At this moment, a still image of the color or fluorescent image stored in the memories 14r, 14g and 14b is displayed on the screen of the TV monitor 25 to confirm the above operation for about a half second, for example, and then the display recovers the (moving) video from the endoscope. A plurality of images can be stored in each of the image memories 14r, 14g and 14b, and still color or fluorescent images can be sequentially stored with each depression of the control button A.

The control button B is a button for displaying on screen of the TV monitor 25 the still color or fluorescent image (still video) stored in the image memories 14r, 14g and 14b. Namely, when video captured by the endoscope 30 or 50 is displayed on the image indicating area 71 of the TV monitor 25, and the control button B is depressed, the still color or fluorescent image stored in the image memories 14r, 14g and 14b is displayed on the image indicating area 71. Further, when a still color or fluorescent image is displayed on the image indicating area 71, and the control button B is depressed, image on the image indicating area 71 is switched to another still image (still video) stored in the image memories 14r, 14g and 14b. The above image switching among the still images stored in the image memories 14r, 14g and 14b, and displayed on the image indicating area 71, is executed in accordance with the stored order of the images. For example, when control button B is depressed while the last stored still image in the image memories 14r, 14g and 14b is displayed on the image indicating area 71, the first stored still image in the image memories 14r, 14g and 14b is redisplayed. This process may be continued repeatedly until the control buttons A and B are simultaneously depressed. When the control buttons A and B are depressed simultaneously, an image displayed on the image indicating area 71 reverts to the normal video (moving image) from either endoscope 30 or 50.

The control button C switches an indicating mode for an image on the screen 70. Each time the control button C is depressed, the display on the screen 70 alternates between a one-image indicating mode (first image-indicating mode), which indicates one image on the screen 70 as shown in FIG. 2, and a two-image indicating mode (second image-indicating mode) which indicates two images on the screen 70 as shown in FIG. 3. On the screen 70, which is depicted in FIG. 3, both normal video (moving image as the live image) from either endoscope 30 or 50, and a still image stored in the image memories 14r, 14g and 14b, are displayed on the image indicating area 73 and 74, together. A hatched portion 75 is a margin area where no image is displayed in the same way as the hatched portion 72 in FIG. 2.

When control button B is depressed while the two-images indicating mode is selected, a still image displayed on the image indicating area 74, is switched to another still image. The above image switching, on the image indicating area 74, among the still images stored in the image memories 14r, 14g and 14b, is executed in accordance with storing order of the images. For example, when control button B is depressed while the last still image stored in the image memories 14r, 14g and 14b is displayed on the image indicating area 74, the first still image stored in the image memories 14r, 14g and 14b is redisplayed.

With reference to FIGS. 1 and 4, a signal processing and switching operation in the electronic endoscope selector is explained as follows:

The RGB component video signals R1, G1 and B1, from the image-signal processor 41 of the image-signal processing unit 40, are input to switching circuits 11r, 11g and 11b respectively, and the synchronization signal T1 from the timing controller 42, is input to a switching circuit 12. Further, a control signal from the system control circuit 43 is input to a system control circuit 21.

In the same way as discussed above, the RGB component video signal R2, G2 and B2, from the image-signal processor 61 of the image-signal processing unit 60, are input to the switching circuits 11r, 11g and 11b respectively, and the synchronization signal T2 from the timing controller 62 is input to the switching circuit 12. Further, a control signal from the system control circuit 63 is input to the system control circuit 21. Note that, as discussed above, the component video signals R2, G2 and B2, from the image-signal processing unit 60, correspond to the three fluorescent images captured during one revolution of the rotating filter 58, and have no relation to the R, G and B color components. However, these three fluorescent images are treated in the same way the images corresponding to the R, G and B color components are treated, thus in the following description, the above three fluorescent images are treated as if they are images of the R, G and B color components.

The switching circuits 11r, 11g, 11b and 12 select a set of output signals between the component signals (R1, G1, B1, T1) and (R2, G2, B2, T2) in accordance with a control signal from the system control circuit 21. The control signal from the system control circuit 21 relates to a control signal from a control panel 22, which is connected to the system control circuit 21, or a control signal from the image-signal processing units 40 or 60.

The synchronization signals from the switching circuit 12 are fed to a timing controller 20. At the timing controller 20, new synchronization signals, which are synchronized to the synchronization signals from the image-signal processing unit 40 or 60, are generated and output. Timing for each circuit in the electronic endoscope selector 10 is driven by the synchronization signals from the timing controller 20. Further, the synchronization signals from the timing controller 20 are fed to the peripheral devices, i.e., the TV monitor 25 and VCR 26, via a cable driver (a driver for signal transmission via a cable) 19, so that each of the peripheral devices is able to synchronize with the electronic endoscope selector 10 and the electronic endoscope unit 40 or 60. Note that, the timing controller 20 is controlled by the system control circuit 21.

On the other hand, the RGB component video signals fed from the switching circuits 11r, 11g and 11b are fed to an A/D converter 13, which has three channels, and converted to digital signals from the analog signals. The digital signals are then fed to the digital processor 15 as R, G, and B image data. At the same time, the RGB image data may be stored in the image memories 14r, 14g and 14b, respectively. The RGB image data are stored in the image memories 14r, 14g and 14b when the control button A is depressed, as described above with reference to FIG. 1 through FIG. 3. Namely, when the control button A of the endoscope 30 (or 50) is depressed, the system control circuit 43 (or 63) of the image-signal processing unit 40 (or 60) outputs control signals to the system control circuit 21. The system control circuit 21 controls the switching circuits 11r, 11g, 11b and 12, in accordance with the control signals from the control panel 22 or control signals from image-signal processing unit 40 (or 60), to switch and select the component signals and to feed the RGB component video signals (which are part of the above selected component signals) to the A/D converter 13 so that the analog signals are converted to digital signals. The A/D converter 13 outputs image signals or image data for the R, G and B to the image memories 14r, 14g, 14b and digital processor 15, and each of the R, G and B image data are stored in the respective image memories 14r, 14g and 14b. The images stored in the image memories 14r, 14g and 14b are output able to the digital processor 15.

In the digital processor 15, image processing for the image data from the A/D converter 13 and image memories 14r, 14g and 14b, is executed, and image data for the TV monitor 25 is provided to the D/A converter 16.

In the one-image indicating mode, the above image processing is applied to image data corresponding to either the video (moving image) signals, fed directly from the A/D converter 13, or the still image signals, which are fed from the image memories 14r, 14g and 14b, so that the image is displayed on the image indicating area 71, arranged in the central part of the screen 70, as shown in FIG. 2. Either video or still image signals are selected for image processing by a signal from the system control circuit 21. Further, image processing for a specific still image, stored in the image memories 14R, 14G and 14B, is also selected by a signal from the system control circuit 21. These control signals are provided in accordance with control signals from the image-signal processing unit, and are further generated in accordance with operations of the control buttons A, B and C on the endoscope.

On the other hand, in the two-image indicating mode, image processing is applied to both the image data that corresponds to the video (moving image) signals, fed directly from the A/D converter 13, and image data that corresponds to the still image signals, fed from the image memories 14r, 14g and 14b, so that the real time video and stored still image are simultaneously displayed on the image indicating areas 73 and 74, as shown in FIG. 3. Note that, selection of the image indicating mode is also executed in accordance with a signal from the system control circuit 21.

Image data generated by image processing at the digital processor 15, are output to a D/A converter 16, which has three channels, each one corresponding to the respective R, G and B data, and converted to analog signals, respectively. The analog converted RGB video signals are fed to respective video-signal processors 17r, 17g and 17b. At the video-signal processors 17r, 17g and 17b, adjustment for a RGB color balance and gamma correction is carried out according the image parameters stored in a memory 24. The values of the image parameters may be set and altered for each electronic endoscope units connected to the electronic endoscope selector 10 by operating the switch group (not shown) arranged on the control panel 22. Namely, in the present embodiment, the image parameters, which are the R, G, B gains for the color balance and gamma factors, are able to be set for each of the endoscope 30 and endoscope 50, so that the image parameters of either image displayed on the screen of the TV monitor 25, are similar or the same. The set image parameters are stored in the memory 24. The system control circuit 21 decides which image parameter to read from the memory 24, in accordance with the selection of the video signals by the switching circuits 11r, 11g, 11b or the image data at the digital processor 15, and then send control signals that correspond to the above readout image parameters to the video-signal processors 17r, 17g, 17b via the D/A converter 23.

The video signals for the R, G and B images, to which RGB color balance and gamma correction were adjusted in the video-signal processor 17r, 17g and 17b, are fed to the TV monitor 25 and VCR 26 via respective cable drivers 18r, 18g and 18b, as the RGB component video signals.

As described above, according to the present embodiment, an operator can easily access a fluorescent image, which is obtained by the endoscope 50, during an examination or operation with the endoscope 30, without continually exchanging the inserted endoscope 30 for the endoscope 50. A preliminary examination can be carried out with the endoscope 50 and the fluorescent still images are then stored in the image memories 14r, 14g and 14b. Endoscope 50 is then replaced with the endoscope 30 and real-time color video and fluorescent (still) images, from the image memories 14r, 14g and 14b, may be alternately or simultaneously displayed on the screen of the TV monitor. Consequently, a comparative display between the fluorescent image and normal color video is facilitated enabling a precise and convenient examination and operation. Moreover, discomfort to the patient is reduced, since the number of endoscope interchanges is decreased.

Furthermore, according to the present embodiment, since the operation for storing a captured image, selecting which image to display on the screen, switching the image indicating modes, etc., are controlled by the control buttons arranged on the endoscope, the operator can easily handle the above operation in parallel with the operation of the endoscope. Since the image parameters are set for each of the electronic endoscope units, images from every electronic endoscope unit may be displayed on the screen of the TV monitor in an appropriate color tone.

Note that, in the present embodiment, although the electronic endoscope unit applying the RGB sequential method and the electronic endoscope unit that captures a fluorescent image by emitting shortwave light are described, other types of electronic endoscope units may be applied. Further, in the present embodiment, although two electronic endoscope units are connected to the electronic endoscope selector, the number of the electronic endoscope units connected to the electronic endoscope selector, may be three or more.

In the present embodiment, the RGB component video signals and synchronizing signals are applied in the electronic endoscope system, however, another type of transmission system may be applied to the system.

In the present embodiment, still images are the images stored in the image memories, though moving images may be stored in the image memories. Further, in the present embodiment, the image memories are mounted inside the electronic endoscope selector, they may be disposed outside the electronic endoscope selector.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2000-002673 (filed on Jan. 11, 2000), which is expressly incorporated herein, by reference, in their entireties.

What is claimed is:

1. An electronic endoscope system, comprising:
    a plurality of electronic endoscopes;
    a storage medium that stores at least one recorded image;
    an image display device that displays images captured by said plurality of electronic endoscopes;
    an image storing processor that stores at least one image captured by one of said plurality of electronic endoscopes, in said storage medium as the recorded image;
    a comparative image displaying processor that executes image signal processing, so that a live image being captured by one of said plurality of electronic endoscopes, and the recorded image stored in said storage medium, are comparatively displayed on a screen of said image display device.

2. The system according to claim 1, further comprising:
    an electronic endoscope selector that selects one electronic endoscope from among said plurality of electronic endoscopes and feeds video signals obtained by said selected electronic endoscope to said image display device, said selected electronic endoscope being switchable to another electronic endoscope,
    wherein the recorded image and the live image are comparatively displayed on said image display device by driving said comparative image displaying processor.

3. The system according to claim 2, wherein said storage medium and said comparative image displaying processor are disposed in said electronic endoscope selector.

4. The system according to claim 2, wherein said electronic endoscope selector comprises a video-signal processor that executes an adjustment for factors relating to a tone of the images displayed on said image display device.

5. The system according to claim 4, wherein the adjustment is executed in accordance with image parameters set for each of said plurality of electronic endoscopes.

6. The system according to claim 5, wherein said electronic endoscope selector comprises an image parameter storing processor that stores the image parameters.

7. The system according to claim 1, wherein said comparative image displaying processor comprises a first image-displaying mode that is able to display the recorded image and the live image, alternately on said screen of said image display device.

8. The system according to claim 1, wherein said comparative image displaying processor comprises a second image-displaying mode that is able to display the recorded image and the live image simultaneously on said screen of said image display device.

9. The system according to claim 1, wherein said plurality of electronic endoscopes comprises at least one control switch in order to control said comparative image displaying processor and said image storing processor.

10. The system according to claim 9, wherein said at least one control switch comprises a first control switch that is to control a storing operation of said image storing processor, so that the image, captured by one of said plurality of electronic endoscopes, is stored in said storage medium as the recorded image.

11. The system according to claim 9, wherein said image storing processor is configured to store a plurality of recorded images in said storage medium, and said at least one control switch comprises a second control switch that selects one of the plurality of recorded images to display the selected recorded image on said screen of said image display device.

12. A The system according to claim 1, wherein said comparative image displaying processor comprises:
    a first image-display mode that displays the recorded image and the live image, alternatively on said screen of said image display device; and
    a second image-display mode that displays the recorded image and the live image, simultaneously on said screen of said image display device.

13. The system according to claim 12, wherein said plurality of electronic endoscopes comprises at least one control switch configured to control said comparative image displaying processor and said image storing processor; and
    wherein said at least one control switch comprises a third control switch to control a switching operation between said first and second image-display modes.

14. The system according to claim 1, wherein the recorded image comprises a still image.

15. The system according to claim 1, wherein the recorded image comprises a moving image.

16. An electronic endoscope selector, comprising:
    a storage medium that stores at least one recorded image;
    a video signal switching processor that selectively switches video signals from among a plurality of video signals, which are being fed from a plurality of electronic endoscopes, so that a selected video signal is fed to an image display device;
    an image storing processor that stores at least one image captured by one of the plurality of electronic endoscopes, in said storage medium as the recorded image; and a comparative image displaying processor that comparatively displays an image of the selected video signal, and the recorded image.

17. The selector according to claim 16, wherein said image storing processor and said comparative image displaying processor are controlled based upon a control signal from one of the plurality of electronic endoscopes.

18. The selector according to claim 16, further comprising a video-signal processor that executes an adjustment for factors relating to a tone of the images displayed on the image display device.

19. The selector according to claim 18, wherein the adjustment is executed in accordance with image parameters set for each of the plurality of electronic endoscopes.

20. The selector according to claim 19, further comprising an image parameter storing processor that stores the image parameters.

21. The selector according to claim 16, wherein the recorded image comprises a still image.

22. The selector according to claim 16, wherein the recorded image comprises a moving image.

* * * * *